United States Patent
Lee et al.

(10) Patent No.: US 9,939,053 B2
(45) Date of Patent: Apr. 10, 2018

(54) ROBOT ARM DRIVING APPARATUS AND ROBOT ARM HAVING THE SAME

(71) Applicant: Samsung Electronics Co., Ltd., Suwon-si (KR)

(72) Inventors: Youn Baek Lee, Suwon-si (KR); Yong Jae Kim, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 401 days.

(21) Appl. No.: 13/855,049

(22) Filed: Apr. 2, 2013

(65) Prior Publication Data
US 2013/0255410 A1    Oct. 3, 2013

(30) Foreign Application Priority Data
Apr. 2, 2012   (KR) .......................... 10-2012-0033695

(51) Int. Cl.
*A61B 1/005*   (2006.01)
*B25J 9/04*    (2006.01)
(Continued)

(52) U.S. Cl.
CPC .......... *F16H 19/08* (2013.01); *A61B 1/0051* (2013.01); *A61B 1/0052* (2013.01);
(Continued)

(58) Field of Classification Search
CPC ... A61B 1/0051; A61B 1/0052; A61B 1/0055; A61B 1/0057; A61B 19/2203;
(Continued)

(56) References Cited

U.S. PATENT DOCUMENTS 2,613,001 A * 10/1952 Green ................... B66C 23/605
212/310
3,190,286 A *  6/1965 Stokes ............... A61B 1/00165
600/146
(Continued)

FOREIGN PATENT DOCUMENTS

CN         1826083 A    8/2006
CN       101026988 A    8/2007
(Continued)

OTHER PUBLICATIONS

Chinese Office Action dated Sep. 25, 2015, issued in corresponding Chinese Application No. 201310113039.X (with translation).

*Primary Examiner* — Timothy J Neal
*Assistant Examiner* — Aaron B Fairchild
(74) *Attorney, Agent, or Firm* — Harness, Dickey & Pierce, P.L.C.

(57) ABSTRACT

A robot arm capable of being driven with a small force while having an enhanced rigidity includes a joint unit formed by stacking a plurality of link modules up against each other, and at least one driving device allowing the joint unit to pivot along at least one axis, wherein the driving device includes a cable disposed to pass through the plurality of link modules a plurality of times, a plurality of multi-turn pulleys configured to change a path of the cable when the cable passes therethrough, such that the cable passes through the plurality of link modules, and a driving unit configured to pull or push the cable such that the joint unit pivots.

20 Claims, 9 Drawing Sheets

(51) Int. Cl.
*B25J 9/06* (2006.01)
*B25J 9/10* (2006.01)
*B25J 18/06* (2006.01)
*F16H 19/06* (2006.01)
*F16H 19/08* (2006.01)
*A61B 17/00* (2006.01)
*A61M 25/01* (2006.01)

(52) U.S. Cl.
CPC .......... *A61B 1/0055* (2013.01); *A61B 1/0057* (2013.01); *B25J 9/065* (2013.01); *B25J 9/104* (2013.01); *B25J 9/106* (2013.01); *B25J 9/1045* (2013.01); *B25J 18/06* (2013.01); *F16H 19/06* (2013.01); *A61B 2017/00323* (2013.01); *A61B 2017/00327* (2013.01); *A61M 25/0136* (2013.01); *A61M 25/0147* (2013.01); *F16H 2019/0695* (2013.01); *Y10T 74/18848* (2015.01)

(58) Field of Classification Search
CPC .. A61B 2019/2242; A61B 2017/00323; A61B 2017/00327; A61B 2034/301; A61B 2034/305; A61B 2034/306; B25J 9/065; B25J 9/104; B25J 9/1045; B25J 9/106; B25J 18/06; Y10S 901/21; F16H 55/36; A61M 25/0136; A61M 25/0147

USPC ...... 74/89.22, 490.01, 490.04; 600/146–152; 604/95.03–95.04, 528; 606/130; 294/111; 901/14–18, 21
See application file for complete search history.

(56) References Cited

U.S. PATENT DOCUMENTS

| | | | |
|---|---|---|---|
| 3,557,780 A * | 1/1971 | Sato ............................ 600/148 |
| 4,494,417 A | 1/1985 | Larson et al. |
| 4,946,380 A * | 8/1990 | Lee ................................ 901/21 |
| 5,462,527 A * | 10/1995 | Stevens-Wright ........................ A61B 18/1492 600/585 |
| 5,479,930 A * | 1/1996 | Gruner et al. ................ 600/146 |
| 6,236,876 B1 * | 5/2001 | Gruner ................ A61B 1/0052 600/146 |
| 6,270,453 B1 | 8/2001 | Sakai |
| 2005/0090809 A1 | 4/2005 | Cooper et al. |
| 2006/0095022 A1 * | 5/2006 | Moll et al. ....................... 606/1 |
| 2008/0216596 A1 | 9/2008 | Madhani et al. |
| 2009/0216083 A1 * | 8/2009 | Durant ................ A61B 1/0057 600/130 |
| 2011/0301751 A1 | 12/2011 | Gao et al. |

FOREIGN PATENT DOCUMENTS

| | | |
|---|---|---|
| CN | 101214138 A | 7/2008 |
| JP | H09-019402 A | 1/1997 |
| JP | 2000-300511 A | 10/2000 |
| KR | 10-2011-0083340 | 7/2011 |

* cited by examiner

ROBOT ARM DRIVING APPARATUS AND ROBOT ARM HAVING THE SAME

CROSS-REFERENCE TO RELATED APPLICATIONS

This application claims the priority benefit of Korean Patent Application No. 10-2012-0033695, filed on Apr. 2, 2012 in the Korean Intellectual Property Office, the disclosure of which is incorporated herein by reference.

BACKGROUND

1. Field

The following description relates to a robot arm driving apparatus, and more particularly, to a robot arm having the same.

2. Description of the Related Art

In the past, an open surgery using an abdominal incision and an open abdomen to perform a surgery in an abdominal cavity was common. Because an open surgery may cause a large amount of pain and require a slow recovery while leaving a scar, numerous studies have been conducted on a minimally invasive surgery.

The minimally invasive surgery refers to a surgery in which the size of an affected area is minimal. The examples of the minimally invasive surgery include a laparoscopic surgery. In the laparoscopic surgery, a plurality of incision holes are formed through the abdomen of a patient, and a laparoscope and a manipulator are inserted through the incisions such that a surgery may be performed. In this regard, the laparoscopic surgery is also referred to as a multi-port surgery.

Because the minimally invasive surgery, which has many advantages when compared to the open surgery, requires a plurality of incision holes, a weakness of the open surgery still remains in the minimally invasive surgery.

Accordingly, many studies have been undertaken on a single port surgery making a single incision hole, and a Natural Orifice Translumenal Endoscopic Surgery (NOTES), which requires making no incision hole.

In the NOTES, a surgical device having flexibility is inserted through a natural orifice, such as a mouth or anus, for example, to access an affected area, and a surgery is performed by manipulating the surgical instrument through the inside of an over tube.

In order to perform the single port surgery and the NOTES, a robot arm needs to be firmly fixed at the affected area while passing along the internal organ and internal body of a patient having a curve. Accordingly, numerous studies have become more active on the structure of a robot arm having flexibility and rigidity.

SUMMARY

Therefore, it is an aspect of the present disclosure to provide a robot arm driven with a small force while having rigidity thereof.

Additional aspects of the disclosure will be set forth in part in the description which follows and, in part, will be obvious from the description, or may be learned by practice of the disclosure.

In accordance with an embodiment of the present disclosure, a robot arm includes a joint unit, and at least one driving device. The joint unit may be formed by stacking a plurality of link modules up against each other. The at least one driving device may allow the joint unit to pivot along at least one axis. The driving device may include a cable, a plurality of multi-turn pulleys, and a driving unit. The cable may be disposed to pass through the plurality of link modules a plurality of times. The plurality of multi-turn pulleys may be configured to change a path of the cable when the cable passes therethrough, such that the cable passes through the plurality of link modules a plurality of times. The driving unit may be configured to pull or push the cable such that the joint unit pivots.

The cable may include a first line and a second line. The first line may be disposed to pass through first parts of the plurality of link modules in a parallel manner a plurality of times. The second line may be disposed to pass through second parts of the plurality of link modules in a parallel manner a plurality of times, the second layer disposed at an opposite side to the first part.

The cable may form a closed loop as the first line is connected to the second line.

The first line and the second line may be connected to each other at the driving unit to form a closed loop.

The joint unit may include a cap module. The cap module may be disposed at an end part of the joint unit and configured to allow the first line to be connected to the second line.

The multi-turn pulley may include an out-in pulley. The out-in pulley may be disposed at an end portion of the joint unit that is far from the driving unit to change the path of the cable.

The multi-turn pulley may include an in-out pulley. The in-out pulley may be disposed at an end portion of the joint unit that is adjacent to the driving unit to change the path of the cable.

The in-out pulley and the out-in pulley may support the cable at different positions, respectively, so that the cable passes through the plurality of link modules a plurality of times.

The plurality of link modules may include a first link module and a second link module. The first link module may be configured to pivot along a first axis. The second link module may be configured to pivot along a second axis perpendicular to the first axis.

The first link module and the second link module may be stacked up against each other while crossing each other, thereby forming the joint unit.

The driving unit may include a first driving unit and a second driving unit. The first driving unit may be configured to allow the first link module to pivot along the first axis. The second driving unit may be configured to allow the second link module to pivot along the second axis.

The cable may include a first cable and a second cable. The first cable may be disposed to be wound around the first driving unit while passing through the first link module a plurality of times. The second cable may be disposed to be wound around the second driving unit while passing through the second link module a plurality of times.

The robot arm may further include an arrangement pulley. The arrangement pulley may be configured to adjust paths of the first cable and the second cable such that the first cable and the second cable are wound around the first driving unit and the second driving unit, respectively.

In accordance with an aspect of the present disclosure, a robot arm includes a plurality of link modules, at least one driving unit, at least one cable and a plurality of multi-turn pulleys. The plurality of link modules may include first parts and second parts provided at an opposite side of the first parts. The at least one driving unit may be configured to perform forward and backward rotation. The at least one cable may be configured to transmit a driving force of the driving unit to the plurality of link modules. The plurality of multi-turn pulleys may be configured to change a path of the cable when the cable passes therethrough. The at least one cable may include a first line disposed to pass through the first part a plurality of times, and a second line disposed to pass through the second part a plurality of times. The first line and the second line may correspond to a single cable.

The cable may include a first cable allowing the link module to pivot along a first axis, and a second cable allowing the link module to pivot along a second axis perpendicular to the first axis.

The first cable and the second cable may be disposed to prevent interference with each other.

In accordance with an aspect of the present disclosure, a robot arm driving apparatus includes at least one driving unit, at least one cable, at least one in-out pulley and at least one out-in pulley. The at least one driving unit may be configured to perform forward and backward rotation. The at least one cable may be configured to rotate by receiving a driving force from the driving unit. The at least one in-out pulley may be configured to support the cable at a position adjacent to the driving unit. The at least one out-in pulley may be configured to support the cable at a position far from the driving unit. The cable may be disposed to be wound between the in-out pulley and the out-in pulley a plurality of times.

The at least one cable may be each provided in one string of cable to form a closed loop.

As described above, a cable is wound a plurality of times among a plurality of multi turn pulleys, while being disposed in a parallel manner, so that a coupling with respect to a joint unit is secured and the driving being transmitted to a driving unit is amplified in rotating a robot arm.

In accordance with an embodiment of the present disclosure, a method for driving a flexible robot arm includes providing a tension force with a cable and a driving unit; routing the cable through a first side of a first link module and a first side of a second link module a plurality of times; routing the cable through a second side of the first link module and a second side of the second link module a plurality of times; and returning the cable to the driving unit.

In accordance with an embodiment of the present disclosure, a method for driving a flexible robot arm includes providing a tension force with a cable and a driving unit; transmitting the tension force through a first side of a first link module; transmitting the tension force through a first side of a second link module; transmitting the tension force to a first pulley; transmitting the tension force through the first side of the second link module; transmitting the tension force through the first side of the first link module; transmitting the tension force to a second pulley; transmitting the tension force through the first side of the first link module; transmitting the tension force through the first side of the second link module; transmitting the tension force through a second side of the second link module; transmitting the tension force through a second side of the first link module; transmitting the tension force to a third pulley; transmitting the tension force through the second side of the first link module; transmitting the tension force through the second side of the second link module; transmitting the tension force to a fourth pulley; transmitting the tension force through the second side of the second link module; transmitting the tension force through the second side of the first link module; and returning the tension force to the driving unit.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
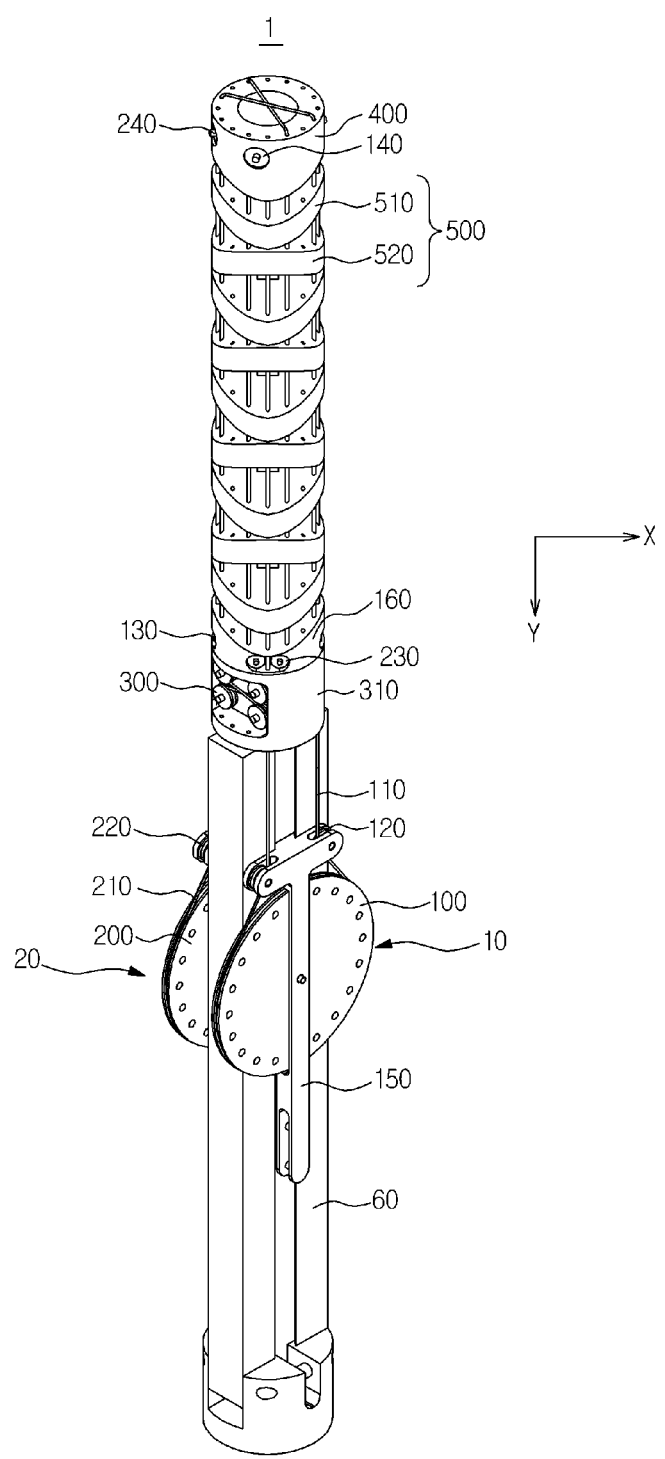
FIG. 1 is a drawing illustrating a robot arm in accordance with an embodiment of the present disclosure.

Reference will now be made in detail to the embodiments of the present disclosure, examples of which are illustrated in the accompanying drawings, wherein like reference numerals refer to like elements throughout.

FIG. 1 is a drawing illustrating a robot arm in accordance with an embodiment of the present disclosure.

Referring to FIG. 1, a robot arm 1 includes a joint unit 500 and driving devices 10 and 20.

The joint unit 500 is formed by linking a plurality of link modules 510 and 520. The link modules 510 and 520 are formed by stacking a first link module 510 and a second link module 520 up against each other. That is, the joint unit 500 is formed in a manner that the second link module 520 may be stacked on the first link module 510, and the first link module 510 may be stacked on the second link module 520. The link modules 510 and 520 may each contain a plurality of holes 511.

A cap unit 400 to accommodate out-in pulleys 140 and 240 among multi-turn pulleys 130, 140, 230, and 240 is disposed at an uppermost end of the joint unit 500, that is, an end portion of the joint unit 500 that is farthest from the driving devices 10 and 20.

A middle unit 160 is disposed at an end of the joint unit 500 opposite to the end, at which the cap unit 400 is disposed, to accommodate in-out pulleys 130 and 230.

An arrangement pulley case 310 is disposed at a lower side of the middle unit 160 to accommodate an arrangement pulley 300.

The driving devices 10 and 20 include at least one cable 110 and 210 passing through the joint unit 500, and driving units 100 and 200 configured to pull or push the cables 110 and 210 such that the cables 110 and 210 pivot.

Although the driving units 100 and 200 are each illustrated in a form of a driving pulley, the present disclosure is not limited thereto. Other members, for example, as a linear actuator, allowing the cables 110 and 210 to move, may be included in the driving units 100 and 200.

The driving unit includes a first driving unit 100 and a second driving unit 200. The first driving unit 100 allows the joint unit 500 to pivot along the X-axis, and the second driving unit 200 allows the joint unit 500 to pivot along the Y-axis. Although the joint unit 500 is provided in a single unit having two degrees of freedom, the present disclosure is not limited thereto. The driving unit may be provided in plurality thereof each having a different degree of freedom for movement. In a case that the joint unit 500 is further added as the above, the driving device is also added as much as the degrees of freedom of the joint unit 500 added.

The joint unit 500 is configured to enable a movement along different axes, but the driving devices 10 and 20 are disposed in parallel to each other due to the shapes thereof.

The first driving device 10 and the second driving device 20 are installed on respective driving unit frames 150 and 250, and the driving unit frames 150 and 250 are installed on a main frame 60. The two driving unit frames 150 and 250 are disposed in parallel to each other while interposing the main frame 60 therebetween, and the driving devices 10 and 20 are disposed in parallel to each other while interposing the main frame 60 therebetween.

The first driving device 10 supports the winding of the first cable 110, and the second driving device 20 supports the winding of the second cable 210.

The first cable 110 is disposed to pass through the joint unit 500, and configured to allow the joint unit 500 to pivot along the X-axis. The second cable 210 is disposed to pass through the joint unit 500, and configured to allow the joint unit 500 to pivot along the Y-axis.

Figure 2:
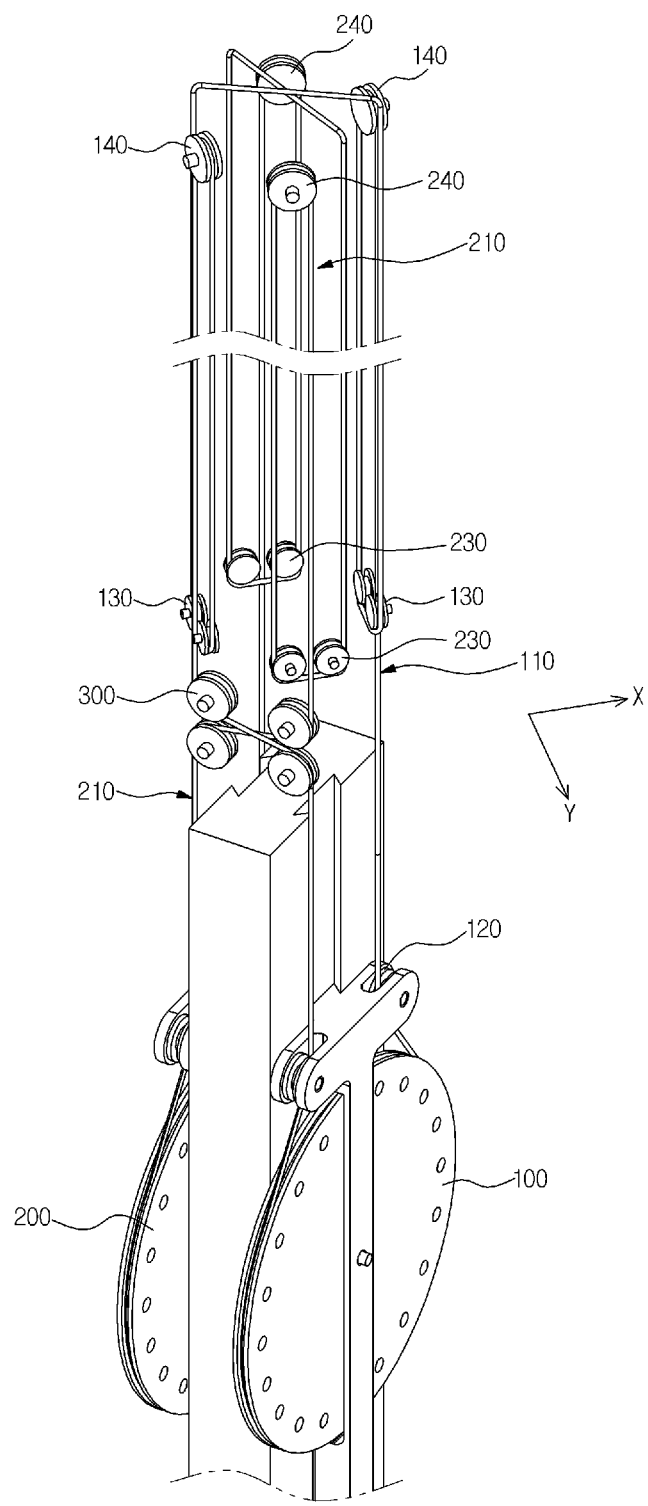
FIG. 2 is a drawing illustrating a driving apparatus for the robot arm of FIG. 1.

FIG. 2 is a drawing illustrating a driving apparatus for the robot arm of FIG. 1.

Referring to FIGS. 1 and 2, the first cable 110 extending from the first driving unit 100 returns to the first driving unit 100 after passing through the first multi-turn pulleys 130 and 140. The first cable 110 is disposed to pass through two end portions of the joint unit 500 that face each other in the X-axis.

The second cable 210 extending from the second driving unit 200 returns to the second driving unit 200 after passing through the second multi-turn pulleys 230 and 240. The second cable 210 is disposed to pass through two end portions of the joint unit 500 that are opposite to each other in the Y-axis.

The first cable 110 and the second cable 210 are each provided in a single unit thereof, and form a single closed loop.

The multi-turn pulleys 130, 140, 230, and 240 for the driving devices 10 and 20 include a total of two out-in pulleys 140 and 240 disposed at an upper side and a total of four in-out pulleys 130 and 230 disposed at a lower side.

The out-in pulleys 140 and 240 change paths of the cables 110 and 210 extending from the driving units 100 and 200 such that the paths of the cables 110 and 210 are oriented toward the respective driving units 100 and 200.

Meanwhile, the in-out pulleys 130 and 230 change paths of the cables 110 and 210 extending from the driving units 100 and 200 such that the paths of the cables 110 and 210 extend in a direction away from the respective driving units 100 and 200.

The first driving device 10 includes a total of two out-in pulleys 140, and the second driving device 20 includes a total of two out-in pulleys 240. The two out-in pulleys 140 are disposed to face each other while the two out-in pulleys 240 are disposed to face each other.

As for the first driving device 10, the two out-in pulleys 140 are disposed to face each other in the X-axis. As for the second driving device 20, the two out-in pulleys 240 are disposed to face each other in the Y-axis.

The first driving device 10 includes a total of four in-out pulleys 130, and the second driving device 20 includes a total of four in-out pulleys 230. The four in-out pulleys 130 are paired to form two sets of in-out pulleys while the two sets of in-out pulleys 130 face each other. The four in-out pulleys 230 are paired to form two sets of in-out pulleys while the two sets of in-out pulleys 230 face each other.

As for the first driving device 10, the two sets of in-out pulleys 130 are disposed to face each other in the X-axis. As for the second driving device 20, the two sets of in-out pulleys 230 are disposed to face each other in the Y-axis.

The first driving unit 100 and the second driving unit 200 are disposed in parallel to each other, but the first cable 110 and the second cable 210 need to be disposed perpendicular to each other. To this end, the paths of the first cable 110 and the second cable 210 need to be changed such that the first cable 110 and the second cable 210 are wound around the first driving unit 100 and the second driving unit 200, respectively. Accordingly, the arrangement pulley 300 is provided. The arrangement pulley 300 is configured to change the extension directions of the first cable 110 and the second cable 210 such that the first cable 110 and the second cable 210 are stably wound around the first driving unit 100 and the second driving unit 200, respectively.

Guide pulleys 120 and 220 are configured to allow the first cable 110 and the second cable 210 to be stably wound without slip on the first driving unit 100 and the second driving unit 200, respectively, while allowing the first cable 110 and the second cable 210 to extend toward the multi-turn pulleys 130, 230, 140, and 240.

The following description will be made in relation to the paths of the cables with reference to FIGS. 3 and 4.

Figure 3:
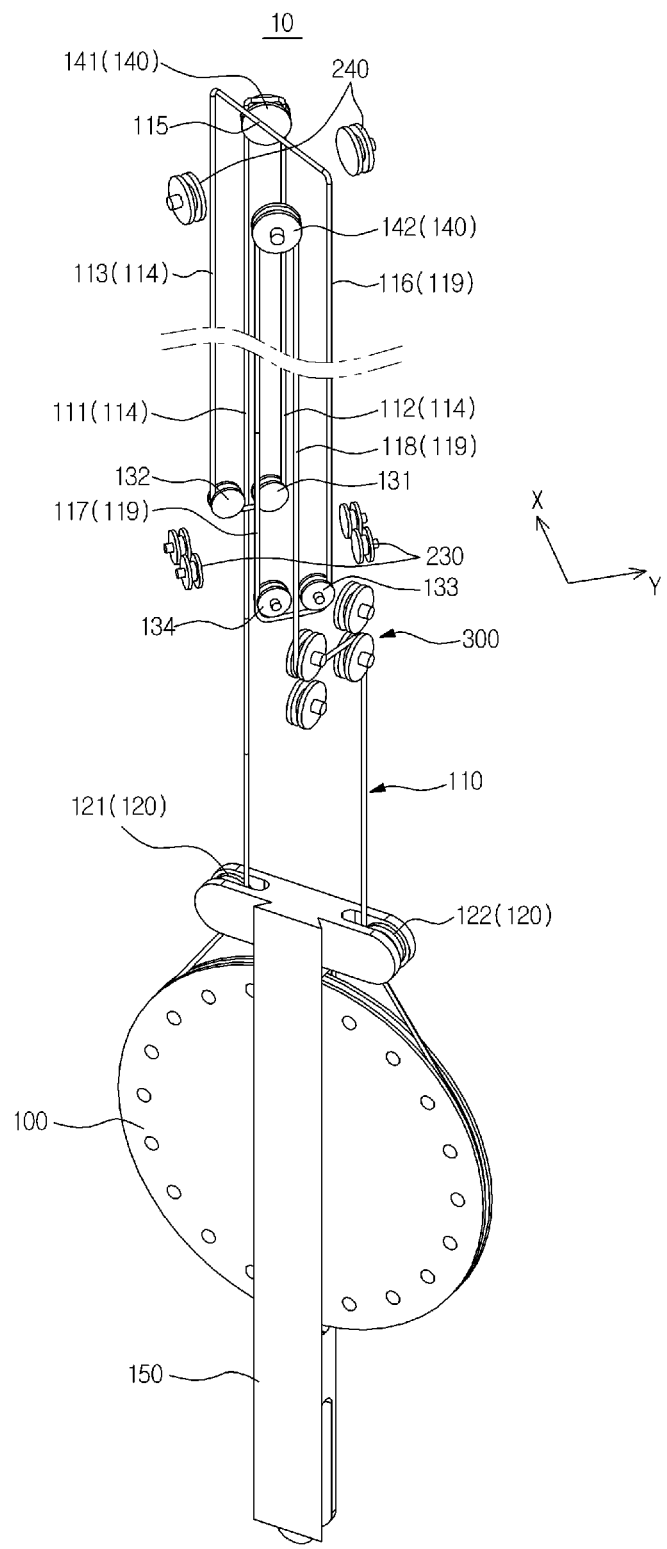
FIG. 3 is a drawing illustrating a configuration of a first driving device for the robot arm of FIG. 1.

FIG. 3 is a drawing illustrating a configuration of the first driving device for the robot arm of FIG. 1.

Referring to FIG. 3, the first driving device 10 includes the first cable 110, the out-in pulley 140, the in-out pulley 130, and the first driving unit 100. The first driving device 10 further includes the arrangement pulley 300 and the guide pulley 120.

Starting from a part of the first cable 110 that extends toward a first guide pulley 121 from the first driving unit 100, the path of the first cable 110 will be described.

A first path 111 refers to a path extending from the first cable 110 via the first guide pulley 121 toward a first out-in pulley 141.

The first cable 110, along the first path 111, extends in a direction away from the first driving unit 100, and after being wound around the first out-in pulley 141, returns toward the first driving unit 100. The path extending downward refers to a second path 112. The second path 112 extends from the first out-in pulley 141 to the first in-out pulleys 131 and 132.

The first cable 110 is wound around the first in-out pulleys 131 and 132, thereby changing the path thereof and extends again in the direction away from the first driving unit 100. The path refers to a third path 113.

The third path 113 extends from the first in-out pulley 131 to the cap unit 400.

A first line 114 refers to including the first path 111, the second path 112, and the third path 113.

The third path 113 enters a path provided at the opposite side to the first line 114 in the X-axis, by passing through a connection path 115 at an upper side.

The connection path 115 returns toward the first driving unit 100. The path refers to a fourth path 116. The fourth path 116 extends from the connection path 115 to second in-out pulleys 133 and 134.

The first cable 110 is wound around the second in-out pulleys 133 and 134, thereby changes the direction thereof and extends in a direction away from the first driving unit 100. The path refers to a fifth path 117. The fifth path 117 extends from the second in-out pulleys 133 and 134 to a second out-in pulley 142.

The first cable 110 is wound around the second out-in pulley 142, thereby changes the direction thereof and returns toward the first driving unit 100. The path refers to a sixth path 118.

The sixth path 118 extends from the second out-in pulley 142 to reach the first driving unit 100 via the second guide pulley 122.

A second line 119 refers to including the fourth path 116, the fifth path 117, and the sixth path 118.

As described above, the first cable 110 forms a closed loop passing both end portions of the joint units 500, while passing through the first path 111 to the sixth path 118.

The first line 114 and the second line 119 may pass through opposite end portions of the joint unit 500, respectively, to allow the joint unit 500 to pivot. That is, the first line 114 and the second line 119 are disposed to face each other in the X-axis.

The first cable 110 forms a path passing through the joint unit 500 a plurality of times, thereby securing the rigidity between the link modules 510 and 520. In addition, the first cable 110 is provided in a single unit thereof, thereby simplifying the overall driving structure.

That is, the first line 114 and the second line 119 correspond to a single cable, so that the degree of movement of the first line 114 may be adjusted to match the degree of movement of the second line 119. Accordingly, the pivot movement of the joint unit 500 is adjusted at a high precision.

Figure 5:
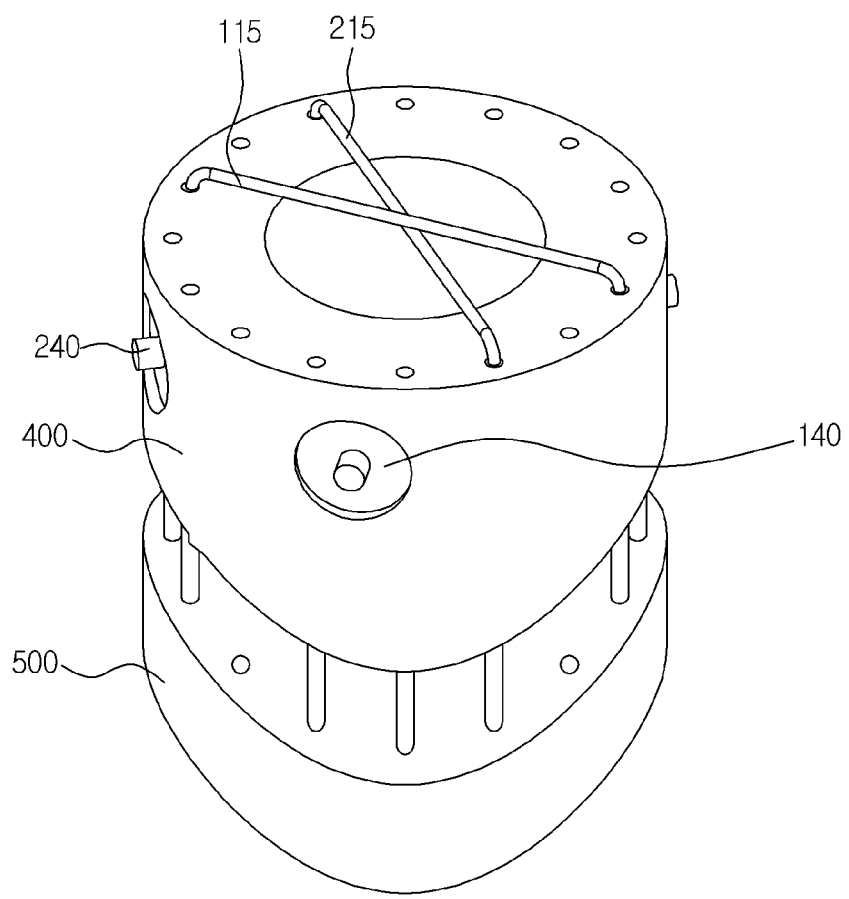
FIG. 5 is an enlarged view of an upper end part of the robot arm of FIG. 1.

FIG. 5 is an enlarged view of an upper end part of the robot arm of FIG. 1.

The extension from the third path 113 via the connection path 115 to the fourth path 116 is illustrated on FIG. 5.

Referring to FIG. 5, the third path 113 extends to the upper end of the cap unit 400 by passing through the cap unit 400. Accordingly, the first cable 110 is bent at the upper end of the cable unit 400, and via the connection path 115, extends to the fourth path 116. The fourth path 116 extends from the upper end of the cap unit 400, and after passing through the cap unit 400, returns toward the driving unit 100.

Figure 4:
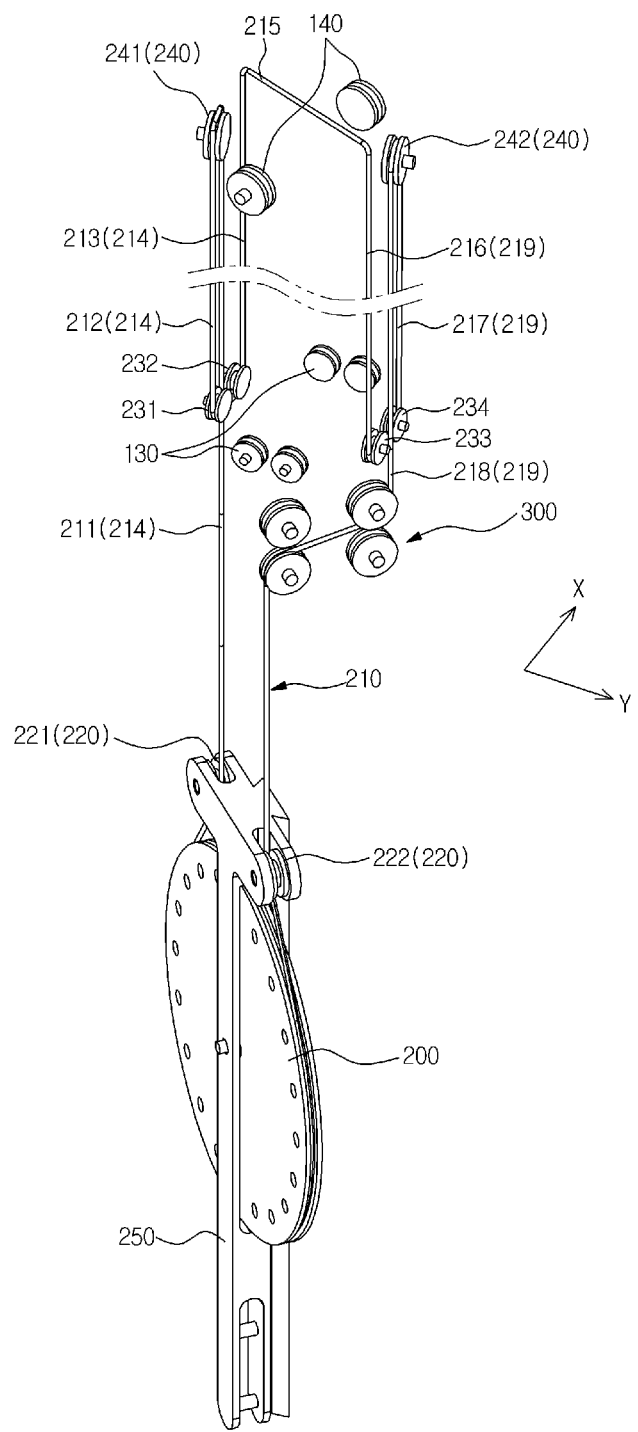
FIG. 4 is a drawing illustrating a configuration of a second driving device for the robot arm of FIG. 1.

FIG. 4 is a drawing illustrating a configuration of the second driving device for the robot arm of FIG. 1.

Referring to FIG. 4, the second driving device 20 includes the second cable 210, the out-in pulley 140, the in-out pulley 130, and the second driving unit 200. The second driving device 20 further includes the arrangement pulley 300 and the guide pulley 220.

Starting from a part of the second cable 210 that extends toward a first guide pulley 221 from the second driving unit 200, the path of the second cable 210 will be described.

A first path 211 refers to a path extending from the second driving unit 200 via the first guide pulley 221 to a first out-in pulley 241.

The second cable 210 is wound around the first out-in pulley 241, changing a path thereof and thus the first path 211 is connected to a second path 212. The second path 212 refers to a path extending from the first out-in pulley 241 to first in-out pulleys 231 and 232.

The second cable 210 is wound around the first in-out pulleys 231 and 232, changing a path thereof and thus the second path 212 is connected to a third path 213. The third path 213 refers to a path extending from the first in-out pulleys 231 and 232 to the cap unit 400.

A third line 214 refers to including the first path 211, the second path 212, and the third path 213.

Referring to FIG. 5, the third path 213 is connected to the connection path 215 at the upper end of the cap unit 400 by passing through the cap unit 400. The connection path 215 is connected to a fourth path 216 at the upper end of the cap unit 400.

The fourth path 216 extends to the lower side of the cap unit 400 by passing through the cap unit 400. The fourth path 216 refers to a path extending from the cap unit 400 to second in-out pulleys 233 and 234.

The second cable 210 is wound around the second in-out pulleys 233 and 234, changing a path thereof and thus the fourth path 216 is connected to a fifth path 217. The fifth path 217 refers to a path extending from the second in-out pulleys 233 and 234 to a second out-in pulley 242.

The second cable 210 is wound around the second out-in pulley 242, changing a path thereof and thus the fifth path 217 is connected to a sixth path 218. The sixth path 218 refers to a path extending from the second out-in pulley 242 via a second guide pulley 222 to the second driving unit 200.

A fourth line 219 refers to including the fourth path 216, the fifth path 217, and the sixth path 218.

Hereinafter, the operation of the robot arm 1 will be described with reference to FIGS. 6 to 9.

Figure 6:
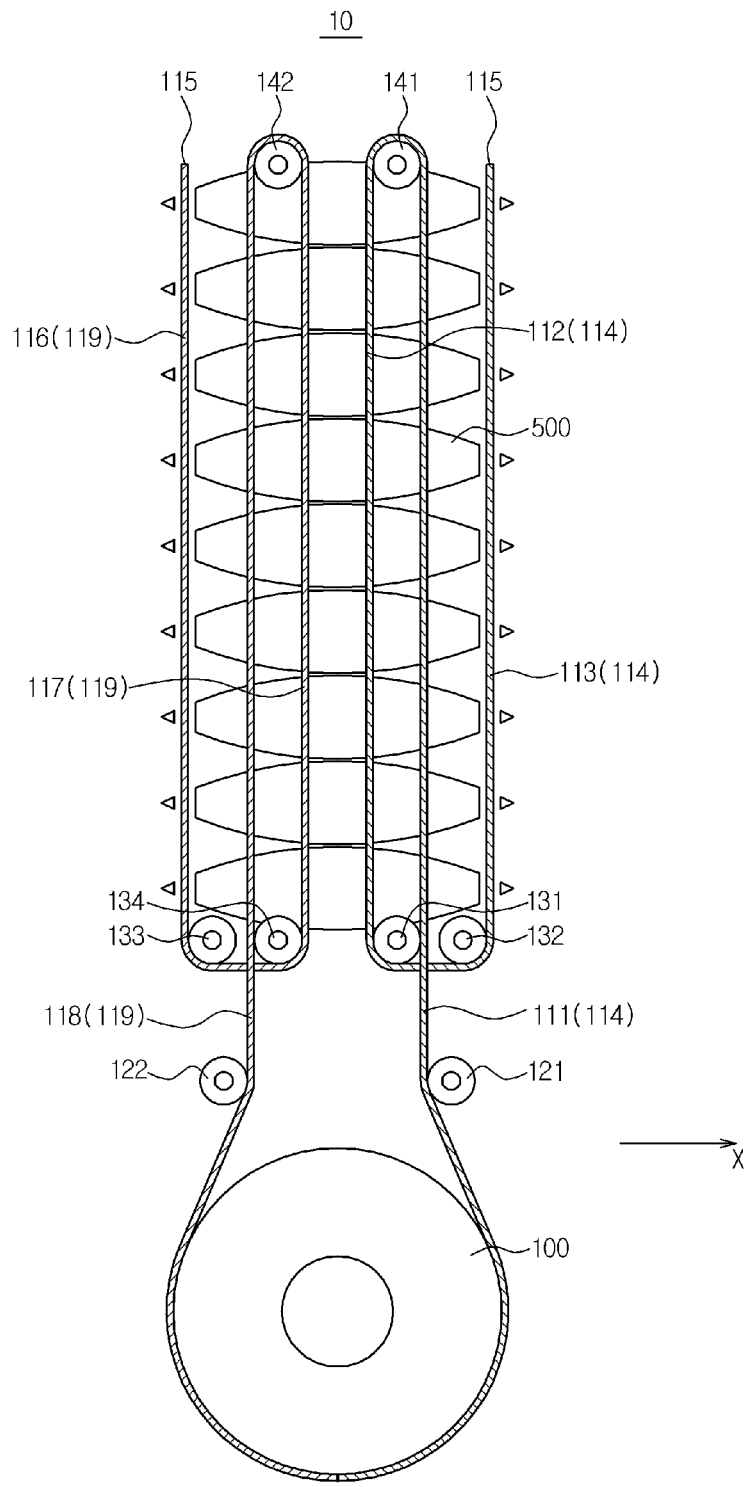
FIG. 6 is a conceptual view illustrating the first driving device of FIG. 3.

FIG. 6 is a conceptual view illustrating the first driving device of FIG. 3.

FIG. 6 is a view illustrating the first driving device 10 in a conceptual aspect. For the sake of convenience for description, the following description will be made in relation to the first driving device 10 rather than the second driving device 20.

Referring to FIG. 6, the first line 114 passes through one end of the joint unit 500, and the second line 119 is disposed at the opposite side to the first line 114 in the X-axis.

As described above, the first line 114 and the second line 119 are each provided in a cable. If the first line 114 is pulled by the rotation of the first driving unit 100, the second line 119 is pushed as much as the amount of the first line 114 is pulled. On the other hand, if the second line 119 is pulled by the rotation of the first driving unit 100, the first line 114 is pushed as much as the amount of the second line 119 is pulled.

In this manner, the joint unit 500 pivots along the X-axis according to the rotation of the first driving unit 100.

If the first driving unit 100 pulls the first line 114, the joint unit 500 pivots in the positive X-axis direction. If the first driving unit 100 pulls the second line 119, the joint unit 500 pivots in the negative X-axis direction.

Each of the first line 114 and the second line 119 is formed by three paths disposed in parallel to each other. Accordingly, when compared to a case of having a single cable or a single path passed through the joint unit 500, the coupling strength of the first link module 510 and the second link module 520 of the joint unit 500 is improved.

Figure 7:
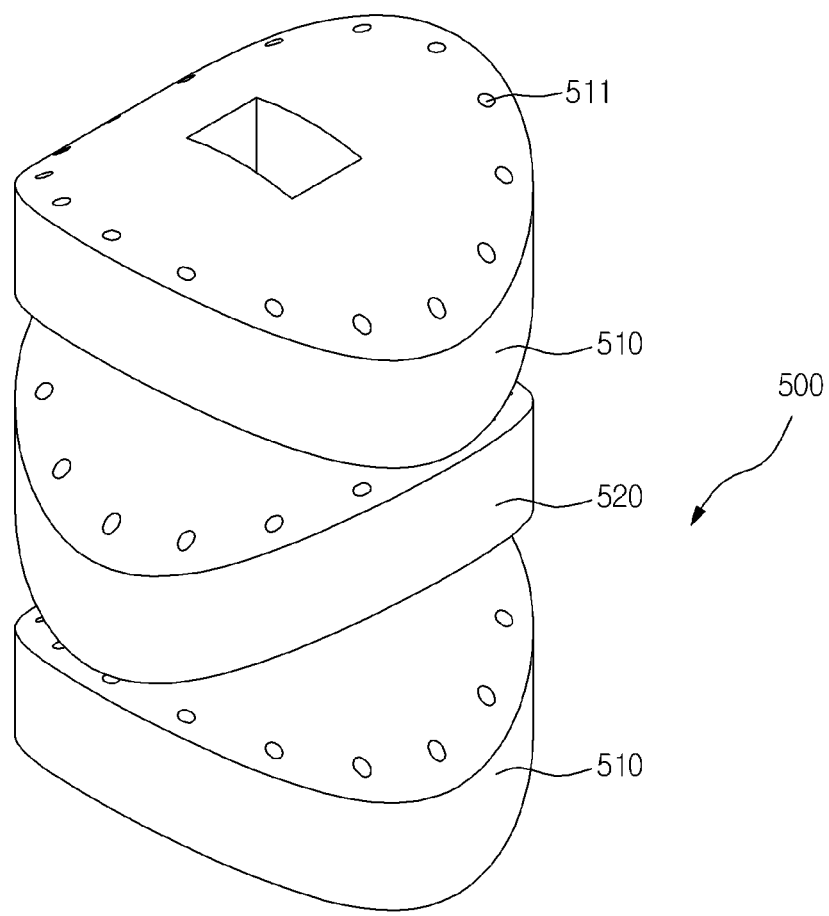
FIG. 7 is an enlarged view of a joint unit of the robot arm of FIG. 1.

FIG. 7 is an enlarged view of a joint unit of the robot arm of FIG. 1.

Referring to FIG. 7, the joint unit 500 includes a first link module 510 and a second link module 520.

The first link module 510 and the second link module 520 are stacked up against each other while crossing each other, thereby forming the joint unit 500.

The first link module 510 and the second link module 520 are provided in the same shape. As shown on the drawing, when the first link module 510 and the second link module 520 have the same shape, the first link module 510 and the second link module 520 are disposed in a twisted manner at an angle of 90 degrees.

Upper surfaces and lower surfaces of the first link module 510 and the second link module 520 may be provided in a curved shape. The first link module 510 and the second link module 520 may easily turn due to the curved surfaces.

However, because the first link module 510 and the second link module 520 are disposed in a twist manner, the first link module 510 rotates in a different direction from the second link module 510.

As shown on the drawing, the first link module 510 and the second link module 520 are disposed such that the pivoting direction of the first link module 510 is perpendicular to the pivoting direction of the second link module 520.

Due to such a difference between the pivoting direction of the first link module 510 and the pivoting direction of the second link module 520, the joint unit 500 pivots in different directions by the first driving device (10 on FIG. 1) and the second driving device (20 on FIG. 2).

Figure 8:
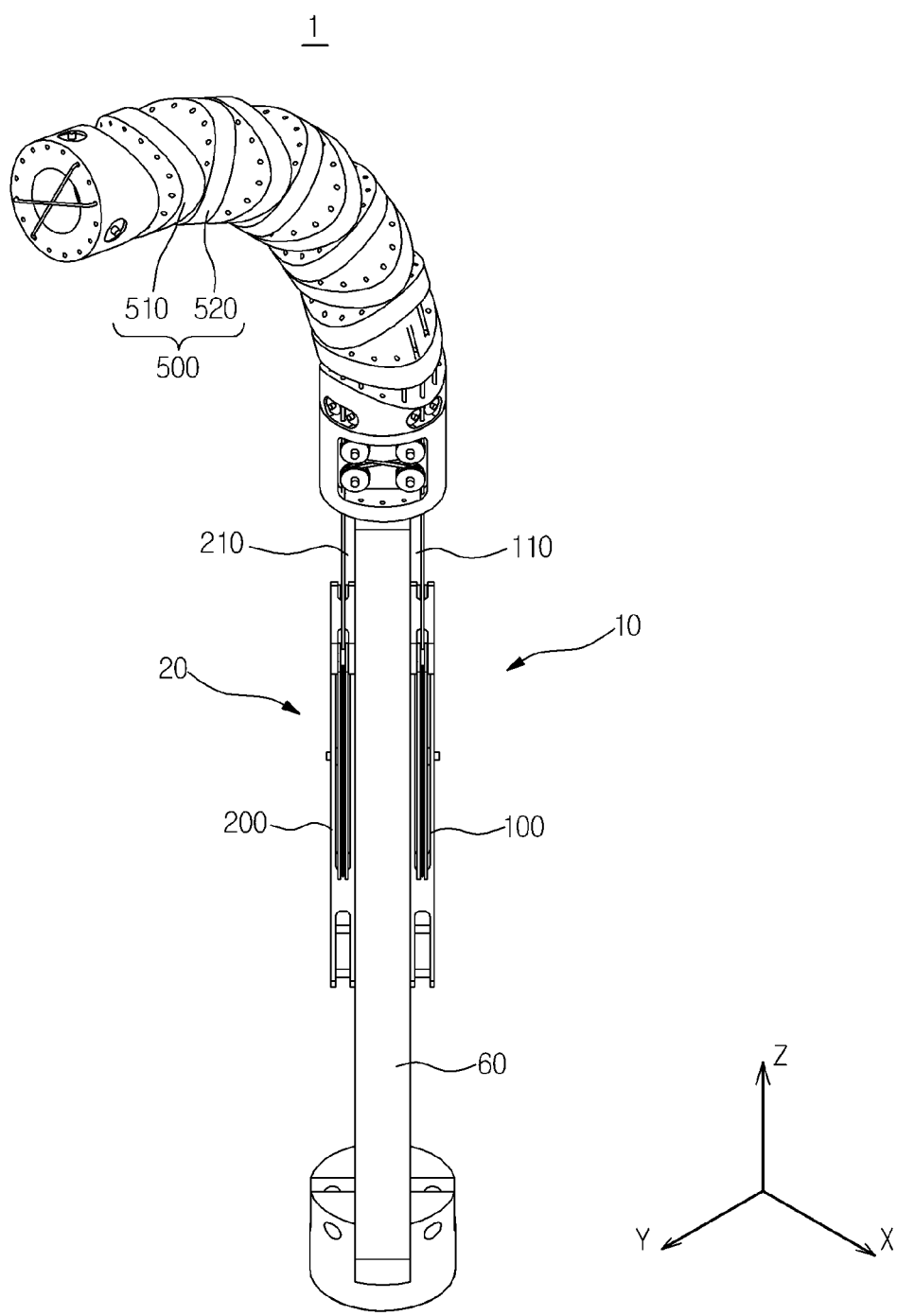
FIGS. 8 and 9 are drawings showing an operation of the robot arm of FIG. 1.
Figure 9:
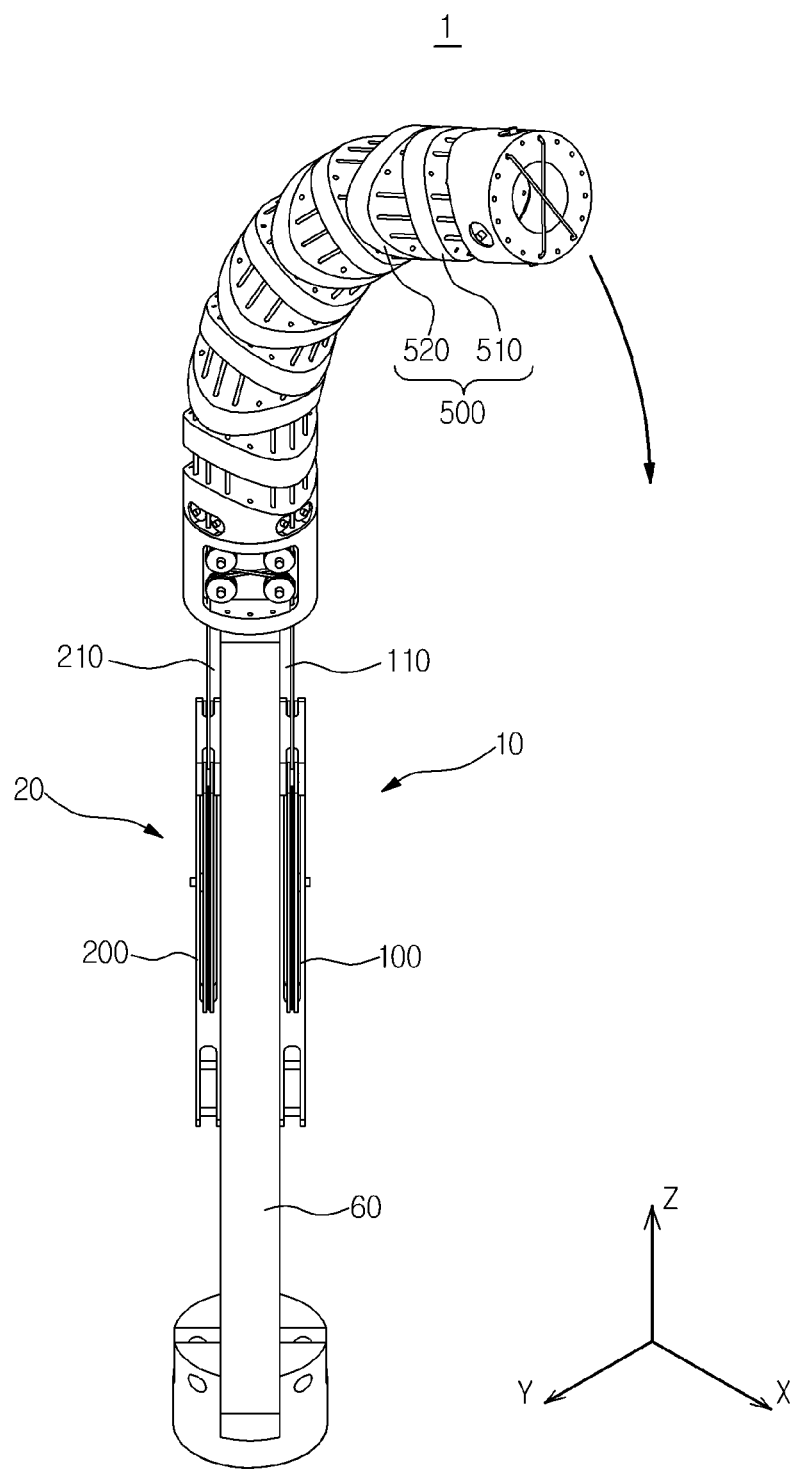

FIGS. 8 and 9 are drawings showing an operation of the robot arm of FIG. 1.

Referring to FIG. 8, the first line (114 on FIG. 3) is pushed as the first driving device 10 rotates, and thus the second line (119 on FIG. 3) is pulled, thereby causing the joint unit 500 to pivot along the X-axis.

Alternatively, if the first line 114 is pulled, and the second line 119 is pushed, the joint unit 500 may pivot in the opposite direction to the direction shown on FIG. 8.

Referring to FIG. 9, the third line (214 on FIG. 4) is pushed as the second driving device 20 rotates, and thus the fourth line (219 on FIG. 4) is pulled, thereby causing the joint unit 500 to pivot along the Y-axis.

Different from the above, if the third line 214 is pulled, and the fourth line 219 is pushed, the joint unit 500 may pivot in the opposite direction to the direction shown on FIG. 9.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An endoscopic medical device, comprising:
    a joint unit including a plurality of stacked link modules;
    at least one first driving device allowing the joint unit to pivot along at least one axis, the at least one first driving device including,
        a first cable and a second cable,
        a plurality of first pulleys configured to change a path of the first cable, such that the first cable passes through the plurality of stacked link modules more than two times in a first direction and passes through the plurality of stacked link modules more than two times in a second direction opposite to the first direction,
        a first driving unit configured to provide a tension force on the first cable such that the joint unit pivots, and
        a second driving unit configured to provide a tension force on the second cable such that the joint unit pivots; and
    arrangement pulleys between the plurality of first pulleys and the first driving unit with respect to a longitudinal direction of the endoscope medical device and configured to adjust paths of the first cable and the second cable such that the first cable and the second cable are wound around the first driving unit and the second driving unit, respectively, the arrangement pulleys including two pairs of facing pulleys that jog the first cable and the second cable in opposite directions across a circumference of the endoscopic medical device, wherein
        the first cable includes a first portion and a second portion that form a continuous loop, the first portion configured to pass from the first driving unit through first parts of the plurality of stacked link modules in a parallel manner more than two times, and the second portion configured to pass from the first driving unit through second parts of the plurality of stacked link modules in a parallel manner more than two times, the second parts being at opposite sides of the plurality of stacked link modules relative to the first parts.

2. The endoscopic medical device of claim 1, wherein the joint unit further comprises:
    a cap module at an end part of the joint unit;
    wherein the first portion of the first cable extends from the first driving unit to the cap module on a first side of the joint unit, and
    wherein the second portion of the first cable extends from the first driving unit to the cap module on a second side of the joint unit.

3. The endoscopic medical device of claim 1, wherein the plurality of first pulleys comprises an outer pulley at an end portion of the joint unit opposite the first driving unit to change the path of the first cable.

4. The endoscopic medical device of claim 3, wherein the plurality of first pulleys comprises an inner pulley at an end portion of the joint unit that is adjacent to the first driving unit to change the path of the first cable.

5. The endoscopic medical device of claim 4, wherein the inner pulley and the outer pulley support the first cable at different positions, respectively, so that the first cable passes through the plurality of stacked link modules the more than two times in the first direction and passes through the plurality of stacked link modules more than two times in the second direction opposite to the first direction.

6. The endoscopic medical device of claim 1, wherein the plurality of stacked link modules comprises:
    a first link module configured to pivot along a first axis; and
    a second link module configured to pivot along a second axis perpendicular to the first axis.

7. The endoscopic medical device of claim 6, wherein the second link module is stacked on the first link module with a 90 degree rotation, thereby forming the joint unit.

8. The endoscopic medical device of claim 6, wherein
    the first driving unit is configured to allow the first link module to pivot along the first axis, and
    the second driving unit is configured to allow the second link module to pivot along the second axis.

9. The endoscopic medical device of claim 8, wherein
    the first cable is wound around the first driving unit while passing through the first link module more than two times, and
    the second cable is wound around the second driving unit while passing through the second link module more than two times.

10. The endoscopic medical device of claim 9, wherein the second cable forms a continuous loop.

11. The endoscopic medical device of claim 1, wherein the plurality of stacked link modules comprises:
    a first link module configured to pivot along a first axis; and a second link module configured to pivot along a second axis different from the first axis.

12. An endoscopic medical device, comprising:
a joint unit including a plurality of stacked link modules;
a cap module at an end part of the joint unit;
at least one first driving device allowing the joint unit to pivot along at least one axis, the at least one first driving device including,
a first cable and a second cable,
a plurality of first pulleys configured to change a path of the first cable, such that the first cable passes through the plurality of stacked link modules more than two times in a first direction and passes through the plurality of stacked link modules more than two times in a second direction opposite to the first direction,
a first driving unit configured to provide a tension force on the first cable such that the joint unit pivots, and
a second driving unit configured to provide a tension force on the second cable such that the joint unit pivots; and
arrangement pulleys between the plurality of first pulleys and the first driving unit with respect to a longitudinal direction of the endoscope medical device and configured to adjust paths of the first cable and the second cable such that the first cable and the second cable are wound around the first driving unit and the second driving unit, respectively, the arrangement pulleys including two pairs of facing pulleys that jog the first cable and the second cable in opposite directions across a circumference of the endoscopic medical device, wherein
the first cable includes a first portion and a second portion forming a continuous section of the first cable from the first driving unit to the cap module and back to the first driving unit, the first portion configured to pass from the first driving unit through first parts of the plurality of stacked link modules in a parallel manner more than two times, and the second portion configured to pass from the first driving unit through second parts of the plurality of stacked link modules in a parallel manner more than two times, the second parts being at opposite sides of the plurality of stacked link modules relative to the first parts.

13. The endoscopic medical device of claim 12, wherein the plurality of first pulleys comprises an outer pulley at an end portion of the joint unit opposite the first driving unit to change the path of the first cable.

14. The endoscopic medical device of claim 13, wherein the plurality of first pulleys comprises an inner pulley at an end portion of the joint unit that is adjacent to the first driving unit to change the path of the first cable.

15. The endoscopic medical device of claim 14, wherein the inner pulley and the outer pulley support the first cable at different positions, respectively, so that the first cable passes through the plurality of stacked link modules the more than two times in the first direction and passes through the plurality of stacked link modules more than two times in the second direction opposite to the first direction.

16. The endoscopic medical device of claim 12, wherein the plurality of stacked link modules comprises:
a first link module configured to pivot along a first axis; and
a second link module configured to pivot along a second axis perpendicular to the first axis.

17. The endoscopic medical device of claim 16, wherein the second link module is stacked on the first link module with a 90 degree rotation, thereby forming the joint unit.

18. The endoscopic medical device of claim 16, wherein
the first driving unit is configured to allow the first link module to pivot along the first axis, and
the second driving unit is configured to allow the second link module to pivot along the second axis.

19. The endoscopic medical device of claim 18, wherein
the first cable is wound around the first driving unit while passing through the first link module more than two times, and
wherein the second cable is wound around the second driving unit while passing through the second link module more than two times.

20. The endoscopic medical device of claim 12, wherein the plurality of stacked link modules comprises:
a first link module configured to pivot along a first axis; and
a second link module configured to pivot along a second axis different from the first axis.

* * * * *